United States Patent [19]
Gay

[11] Patent Number: 5,639,618
[45] Date of Patent: Jun. 17, 1997

[54] METHOD OF ISOLATING A LINEAGE SPECIFIC STEM CELL IN VITRO

[75] Inventor: David A. Gay, San Diego, Calif.

[73] Assignee: Plurion, Inc., Atlanta, Ga.

[21] Appl. No.: 242,547

[22] Filed: May 13, 1994

[51] Int. Cl.$^6$ .............................. G01N 33/53; C12N 5/02; C12N 5/06; C12N 5/10

[52] U.S. Cl. .............................. 435/7.21; 435/2; 435/7.1; 435/7.2; 435/6

[58] Field of Search .................. 435/2, 172.3, 240.1, 435/240.2, 240.21, 7.1, 7.21, 7.2

[56] References Cited

PUBLICATIONS

Shen et al. Int. J. Dev. Biol. 36:465–476 (1992).
Hermiston et al. PNAS 90:8866–8870 (1993).
Reddy et al. PNAS 89:6721–6725 (1992).
Biesecker and Emerson, "Interleukin–6 is a Component of Human Umbilical Cord Serum and Stimulates Hematopoiesis in Embryonic Stem Cells in vitro" *Exp. Hematology* 21:774–778 (1993).
Chisaka, O. and Capecchi, M.R., "Regionally Restricted Developmental Defects Resulting from Targeted Disruption of the Mouse Homeobox Gene Hox-1.5" *Nature* 350:473–479 (1991).
Dinsmore et al., "High Efficiency Differentiation of Mouse Embryonic Stem Cells into Either Neurons or Skeletal Muscle in vitro" Keystone Symposium (Abstract H111) *J. Cell. Biochem.* Supplement 18A:177 (1994).
Fleming et al., "Functional Heterogeneity is Associated with the Cell Cycle Status of Murine Hematopoietic Stem Cells" *J. Cell Biol.* 122:897–902 (1993).
Groves et al., "Repair of Demyelinated Lesions by Transplantation of Purified O–2A Progenitor Cells" *Nature* 362:453–455 (1993).
Hooper et al., "HPRT–Deficient (Lesch–Nyhan) Mouse Embryos Derived from Germline Colonization by Cultured Cells" *Nature* 326:292–295 (1987).
Jones et al., "Separation of Pluripotent Hematopoietic Stem Cells from Spleen Colony–Forming Cells" *Nature* 347:188–189 (1990).
Jones and Watt, "Separation of Human Epidermal Stem Cells from Transit Amplifying Cells on the Basis of Differences in Integrin Function and Expression" *Cell* 73:713–723 (1993).
Keller et al., "Hematopoietic Commitment During Embryonic Stem Cell Differentiation in Culture" *Mol. Cell. Biol.* 13:473–486 (1993).

Kim and Smithies, "Recombinant Fragment Assay for Gene Targeting Based on the Polymerase Chain Reaction" *Nucleic Acids. Res.* 16:8887–8903 (1988).
Lillien and Raff, "Differentiation Signals in the CNS: Type–2 Astrocyte Development in vitro as a Model System" *Neuron* 5:111–119 (1990).
Lufkin et al., "Disruption of the Hox–1.6 Homeobox Gene Results in Defects in a Region Corresponding to its Rostral Domain of Expression" *Cell* 66:1105–1119 (1991).
Mansour et al., "Introduction of a LacZ Reporter gene into the Mouse int–2 Locus by Homologous Recombination" *Proc. Natl. Acad. Sci. USA* 87:7688–7692 (1990).
Matsui et al., "Derivation of Pluripotential Embryonic Stem Cells from Murine Primordial Germ Cells in Culture" *Cell* 70:841–847 (1992).
McKay, R., "The Origins of Cellular Diversity in the Mammalian Central Nervous System" *Cell* 58:815–821 (1989).
McMahon et al., "The Midbrain–Hindbrain Phenotype of Wnt–1$^-$/Wnt–1$^-$ Mice Results from Stepwise Deletion of engrailed–Expressing Cells by 9.5 Days Postcoitum" *Cell* 69:581–595 (1992).
Ott et al., "Use of Recombinant Embryonic Stem Cells to Isolate Neural Stem Cells" Keystone Symposium (Abstract H222) *J. Cell. Biochem.* Supplement 18A:187 (1994).
Patterson, P., "Control of Cell Fate in a Vertebrate Neurogenic Lineage" *Cell* 62:1035–1038 (1990).
Porteus et al., "Isolation and Characterization of a Novel cDNA Clone Encoding a Homeodomain That is Developmentally Regulated in the Ventral Forebrain" *Neuron* 7:221–229 (1991).

(List continued on next page.)

*Primary Examiner*—Lila Feisee
*Assistant Examiner*—Phillip Gambel
*Attorney, Agent, or Firm*—Needle & Rosenberg, P.C.

[57] ABSTRACT

The present invention provides a method of isolating a lineage specific stem cell in vitro, comprising a) transfecting a pluripotent embryonic stem cell with a construct comprising a regulatory region of a lineage specific gene operably linked to a DNA encoding a reporter protein, b) culturing the pluripotent embryonic stem cell under conditions such that the pluripotent embryonic stem cell differentiates into a lineage specific stem cell and c) separating the cells which express the reporter protein from the other cells in the culture, the cell which expresses the reporter protein being an isolated lineage specific stem cell. A lineage specific stem cell can also be identified utilizing this method.

9 Claims, No Drawings

PUBLICATIONS

Price et al., "A Mouse Gene Related to distal-less Shows a Restricted Expression in the Developing Forebrain" *Nature* 351:748–751 (1991).

Resnick et al., "Long-Term Proliferation of Mouse Primordial Germ Cells in Culture" *Nature* 359:550–551 (1992).

Reynolds and Weiss, "Generation of Neurons and Astrocytes from Isolated Cells of the Adult Mammalian Central Nervous System" *Science* 255:1707–1710 (1992).

Roelink, H. and Nuse, R., "Expression of Two Members of the Wnt Family During Mouse Development–Restricted Temporal and Spatial Patterns in the Developing Neural Tube" *Genes Dev.* 5:381–388 (1991).

Schmitt et al., "Hematopoietic Development of Embryonic Stem Cells in vitro: Cytokine and Receptor Gene Expression" *Genes and Develop.* 5:728–740 (1991).

Simeone et al., "Nested Expression Domains of Four Homeobox Genes in Developing Rostral Brain" *Nature* 358:687–690 (1992).

Simeone et al., "Two Vertebrate Homeobox Genes Related to the Drosophila empty spiracles Gene are Expressed in the Embryonic Cerebral Cortex" *EMBO J.*

Snodgrass et al., "Embryonic Stem Cells and in vitro Hematopoiesis" *J. Cell. Biochem.* 49:225–230 (1992).

Stemple and Anderson, "Isolation of a Stem Cells for Neurons and Glia from the Mammalian Neural Crest" *Cell* 71:973–985 (1992).

Wagner, E., "On Transferring Genes into Stem Cells and Mice" *EMBO J.* 9:3025–3032 (1990).

Wolswijk and Noble, "Identification of an Adult-Specific Glial Progenitor Cell" *Development* 105:387–400 (1989).

METHOD OF ISOLATING A LINEAGE SPECIFIC STEM CELL IN VITRO

BACKGROUND OF THE INVENTION

Throughout this application various publications are referenced within parentheses. The disclosures of these publications in their entireties are hereby incorporated by reference in this application in order to more fully describe the state of the art to which this invention pertains.

1. Field of the Invention

This invention relates to pluripotent stem cells and methods for isolating more committed progenitor cells from the pluripotent stem cells.

2. Background Art

Stem cells are undifferentiated, or immature cells that are capable of giving rise to multiple, specialized cell types and ultimately to terminally differentiated cells. These terminally differentiated cells comprise the fully functional organs and tissues within the adult animal and are the end product of embryonic development. Stem cells have two main characteristics. First, unlike any other cells, they are capable of dividing and differentiating into many different mature cell types within the body. Second, they are also able to renew themselves so that an essentially endless supply of mature cell types can be generated when needed. Because of this capacity for self-renewal, stem cells are therapeutically useful for the regeneration and repair of tissues. In contrast, terminally differentiated cells are not capable of self-renewal and are thus not capable of supporting regeneration and repair of damaged or diseased tissue.

The potency of a stem cell is measured by the number of different cell types it can ultimately produce. The most potent stem cell is the pluripotent stem cell (PSC) which can give rise to all cell types of the body (Wagner, E.; Matsui et at.; Resnick et al.). Other stem cells exist and include multipotent stem cells which give rise to two or more different cell types. For example, the multipotent hematopoietic stem cell is capable of giving rise to all cell types of the blood system (Jones et al.; Fleming et al.). Other known multipotent stem cells include a neuronal stem cell and a neural crest stem cell (Reynolds and Weiss; Stemple and Anderson). Bipotential stem cells are also considered multipotent stem cells since they give rise to more than one cell type. Specific examples of bipotential stem cells include the O-2A progenitor (Lillien and Raff; McKay, R.; Wolswijk and Noble) and the sympathoadrenal stem cell (Patterson, P. H.). There is one example of a monopotent stem cell, the epidermal stem cell (Jones and Watt).

The usefulness of stem cells for tissue regeneration and repair has been shown in several systems. For example, grafting of the hematopoietic stem cell has been shown to rescue an animal which has had its bone marrow subjected to lethal doses of radiation (Jones et al., supra). The O-2A progenitor has also been shown to remyelinate spinal cord neurons that have been chemically demyelinated (Groves et at.).

However beneficial these specific stem cells are, they still exhibit several practical drawbacks which limit their commercial development for biomedical applications. One disadvantage is their limited potency for developing into a broad range of cell lineages and tissues. Only the hematopoietic stem cell is capable of producing most cells within a tissue lineage, the other exhibit a very narrow range of developmental potential. Another disadvantage is the origin of the source material. Most neuronal stem cells have been isolated from newborn or early stage fetal tissue. The limited potency of these stem cells requires the independent isolation and maintenance of each cell type which is to be used for a specific application. Thus, the isolation, characterization and commercial usefulness of stem cells with other potentials will depend on the availability of large amounts of source material.

With the availability of a pluripotent stem cell, these disadvantages can be overcome if the pluripotent cell can be differentiated into more committed stem and progenitor cells. Differentiation into a stem cell with a desired potency and lineage specificity would allow an unlimited supply of source material and would also allow the treatment of a broad range of diseases due to the pluripotent nature of the stem cell. Such directed differentiation into a desired cell lineage would be very efficient and extremely cost effective for the commercial development of cellular therapeutics. However, because there are numerous differentiation pathways and points of commitment, and because the inductive effects are very complicated in the developing embryo, such directed differentiation of the pluripotent stem cell has not been accomplished in vitro.

To overcome the above limitations, those skilled in the art have resorted to time consuming experimentation or indirect methodologies in order to understand stem cell differentiation pathways and to isolate, through a series of in vitro and in vivo manipulations, more committed progenitor cells. For example, one of the most characterized stem cells is the bipotential 0-2A progenitor. It has been known for many years that this stem cell is capable of differentiating in vitro into either oligodendrocytes or type-2 astrocytes. However, it was only in recent years that the combination of growth factors needed to direct the differentiation down either pathway was fully understood. The sympathoadrenal stem cell is another such example where time consuming experimentation was necessary in order to understand its differentiation pathway. Although the differentiation pathways of these two bipotential stem cells are the most well characterized, the fact that it still took many years to understand their pathway exemplifies the problem of directed differentiation in vitro to obtain more committed progenitor or terminally differentiated cells.

There are also examples of the in vitro differentiation of multipotent and pluripotent stem cells. ES cells derived from blastocyst and post-implantation embryos can be allowed to uncontrollably differentiate into aggregates and embryoid bodies of terminally differentiated cells. Terminally differentiated cells within the aggregates and embryoid bodies comprise various cell types including extraembryonic endoderm, spontaneously contracting muscle, nerve and endothelial and fibroblast-like cells. ES cells can also be allowed to differentiate into cultures containing either neurons or skeletal muscle (Dinsmore et al.), or hematopoietic progenitors (Keller et al.; Biesecker and Emerson; Snodgrass et al.; Schmitt et al.). However, in none of these examples is the differentiation of the pluripotent stem cell directed down a particular pathway. Instead, they are allowed to differentiate randomly into a mixed population of terminally differentiated cells. Thus, there is no means of isolating a substantially pure population of progenitor cells of a desired cell lineage.

In order to obtain specific cell lineages differentiated from the pluripotent stem cell, those skilled in the art have relied on in vivo mechanisms to direct the differentiation into specific cell lineages. For example, (Otl et at., 1994), have described a method for isolating stem cells of the neuronal lineage after modifying pluripotent stem cells with a reporter construct and then reintroducing them into an early stage embryo. The reporter construct is expressed during neurogenesis and cells expressing the reporter gene are dissected out and placed in culture. Through in vivo mechanisms, this method allows for the isolation of cells committed to the neuronal lineage but, again, the dissected cells once placed in culture proceed to terminal differentiation.

Thus, there exists a need for a rapid method to differentiate and isolate more committed progenitor cells directly from stem cell cultures in vitro without undue experimentation. The present invention satisfies this need and provides related advantages as well.

SUMMARY OF THE INVENTION

The present invention provides a method of isolating a lineage specific stem cell in vitro, comprising:

a. transfecting a pluripotent embryonic stem cell with a construct comprising a regulatory region of a lineage specific gene operably linked to a DNA encoding a reporter protein;

b. culturing the pluripotent embryonic stem cell under conditions such that the pluripotent embryonic stem cell differentiates into a lineage specific stem cell; and c. separating the cells which express the reporter protein from the other cells in the culture, the cell which expresses the reporter protein being an isolated lineage specific stem cell. A lineage specific stem cell can also be identified utilizing this method.

DETAILED DESCRIPTION OF THE INVENTION

As used herein, "lineage specific stem cell" means a stem cell which is less potent than the pluripotent embryonic stem cell. In other words, the lineage specific stem cell has become developmentally committed to be a particular type of stem cell. For example, the pluripotent embryonic stem cell can be induced to be a neuronal stem cell. The neuronal stem cell can produce only neuronal cells. Thus, the cell is committed to the neuronal lineage and is a "lineage specific stem cell."

As used here, "pluripotent embryonic stem cell" means a cell which can differentiate into any normal cell type including germ cells. Pluripotent embryonic stem cells are also referred to as embryonic germ cells depending on the method of isolation.

As used herein, "transfecting" means any manner of introducing a DNA construct into a cell for expression of the construct. Thus, transfection includes electroporation, lipofection, calcium phosphate mediated, DEAE dextran and the like.

"Construct" as used herein means any vector, such as a plasmid, phage or cosmid to which the DNA encoding the reporter protein and the regulatory region of a lineage specific gene have been inserted. The regulatory region is "operably linked" to the DNA encoding the reporter gene. Operably linked means the sequences are attached such that the reporter protein can be expressed in the cell and used as a means to isolate the cell. Various constructs can be created which are suitable for lineage specific stem cell isolation (Sambrook et at. and Ansubel et al.).

The "regulatory region" is the DNA which regulates the binding of transcription factors, including tissue specific and developmental state specific transcription factors, and controls the initiation of transcription. The size of the region depends on the lineage specific gene selected.

The methods encompassed by the technology entail tagging the pluripotent stem cells prior to differentiation with a reporter gene under the control of developmental and lineage specific enhancers. The type of reporter gene employed will depend on the desired goal of the experiment. For example, if it is necessary to follow the differentiation pathway of a specific lineage, or, to test the developmental specificity of the enhancer, then a reporter construct which allows tracking by visual observation is used in conjunction with a lineage specific enhancer (i.e., histochemistry). Typically, this experimental design is used for tracking and characterization of cell lineages and differentiation branch points. However, once lineages are characterized, this same system can be used for the isolation of lineage and stage specific stem cells by simply substituting the type of reporter gene from a histochemical marker to a surface membrane protein. Enhancer specificity will direct expression of the surface protein at the desired stage of isolation and fluorescent activated cell sorting (FACS) will allow the efficient isolation of the desired stem cell. Other immunological separation techniques such as panning may also be applicable for stem cell isolation.

A significant number of genes and their enhancers are known which direct the developmental and lineage specific expression of endogenous genes. The major candidate genes for early neuronal events such as floor plate induction are known. Lineage specificity of other genes is described further below. Therefore, the enhancer that will be used for expression will depend on what stem cell lineage and what stage of development is desired. In addition, as more detail is understood on the finer mechanistic distinctions of lineage specific expression and stem cell differentiation, it can be incorporated into the experimental protocol to fully optimize the system for the efficient isolation of a broad range of desired stem cells.

This technology allows the discovery and isolation of more restricted stem cells and committed progenitors for essentially any lineage in which there are characterized markers. There are several ways to use the molecular tagging method to isolate the lineage specific stem cell, or a committed progenitor within the same lineage and near the same stage of development. One alternative is to isolate the underrepresented population of lineage specific stem cells from a larger population of many cell types. The other alternative is to direct the differentiation of the pluripotent stem cell down the appropriate pathway (e.g., neuronal) to first enrich for a population of lineage specific stem cells. This latter alternative also ensures that short-range signalling which may be necessary for lineage specific stem cell formation is retained within the population. The advantage of the first approach is that it has the capabilities to rapidly obtain the desired cell.

Conditions which can be used to differentiate the pluripotent embryonic stem cell into various lineage specific stem cells is known in the art. For example, pluripotent embryonic stem cells can be allowed to aggregate in culture. Once the cells aggregate the natural communications between the cells causes certain of the cells to begin to differentiate down a particular lineage. The lineage specific cells can be separated at this point or, depending on the desired lineage, the aggregates can be allowed to form embryoid bodies. The lineage specific stem cells can then be isolated from the aggregates or embryoid body depending on the desired developmental stage of the stem cell.

Alternatively, the conditions used to differentiate the pluripotent embryonic stem cell can be performed by the addition of growth factors to the pluripotent embryonic stem cells in culture. These factors cause the cells to differentiate down a particular lineage depending on the growth factor added. For example, the factors which cause a pluripotent embryonic stem cell to differentiate into a hematopoietic stem cell are known to be contained in plasma derived serum (Keller et at.). The serum or isolated factors from the serum can, for example, be utilized to direct the pluripotent embryonic stem cell down the hematopoietic lineage.

Many methods are known in the art to separate a cell type based on the expression of a marker protein (Sambrook et al.). In a presently preferred embodiment, Fluorescent Activated Cell Sorting (FACS) is utilized (Fleming et al.). Various reporter proteins can be utilized including, for example, LacZ and proteins expressed on the cell surface. Depending on the marker utilized, various detecting methods can be utilized, e.g., immunoaffinity procedures, fluorescence, enzymes and the like.

Pluripotent embryonic stem cells can be obtained from established mouse cell lines (Hooper et at., 1987) or by following the methods set forth in Matsui et al. (1992). The method of Matsui et al. allows for the establishment of human pluripotent embryonic stem cells by utilizing the same methods substituting human growth and human fetal material of between six and twelve weeks.

The following example sets forth a specific embodiment of the invention. It should be recognized that other lineage specific regulatory regions from genes such as Dlx (Porteus et al.), Nlx (Price et al.), Emx (Simeone et al. *EMBO J.* 1992), Wnt (Roelink and Nuse), En (McMahon et al.), Hox (Chisaka and Capecchi; Lufkin et al.), acetylcholine receptor β chain (ACHRβ) (Otl et al.) and the like can be substituted for Otx (Simeone et al. *Nature* 1992; Otl et al.). Likewise, various reporter proteins, culture conditions and isolation methods can be substituted without departing from the scope of the invention.

EXAMPLE I

Construction of Stable PSC Lines and Isolation of Lineage Specific Neuronal Stem Cells This Example shows the construction of PSC lines and isolation of neuronal specific stem cells that express a reporter gene under the control of a developmentally stage specific regulatory region of an early neuronal marker.

A. Construction of Stable Lines from Blastocyst Derived ES Cells

ES cell lines are constructed to express a reporter construct under the control of the Otx2 regulatory region. Otx2 is an early marker of neurogenesis. Differentiation into the neuronal lineage therefore results in the activation of the Otx2 regulatory region and biosynthesis of the reporter protein. The reporter protein used for isolation of early neuronal stem cells is the β-chain of the interleukin-2 (IL-2) receptor. This receptor was chosen because it is naturally expressed on the cell surface as a transmembrane protein and because specific antibodies are commercially available to the receptor. Expression of the IL-2 receptor on the surface allows isolation of the neuronal stem cells only after they have committed to the neuronal differentiation pathway.

The ES cell line used to construct the stable cell line is E14TG2a which was originally established by Hooper et al. (1987). ES cells are routinely cultured in DME supplemented with 15% FCS, 0.1 mM β-mercaptoethanol and 1,000 U hLIF on gelatin-coated plates. LIF is purchased from R&D Systems (Minneapolis, Minn.).

To construct the reporter construct, which is also a targeting vector for homologous recombination, the vector contains two arms of homology to the IL-3 receptor gene. The 5' arm corresponds to the first coding exon of the IL-2 receptor and the 3' arm corresponds to the most 5' sequences of the 5' untranslated region sequence and regulatory region. Inserted upstream from the 5' arm and in frame with the ATG initiation codon is the Otx2 regulatory region. Also, included as part of the insert is the neomycin resistance gene (neo$^R$) which is obtained from pMCIneopolA (Stratagene, La Jolla, Calif.). The modified Herpes simplex virus thymidine kinase gene, HSV-tk, (Mansour et al.) is added to the 3' end of the IL-2 receptor sequences, followed by the Bluescript vector (Stratagene). The final construct is termed OtxIL2R.

OtxIL2R is introduced into E14TG2a cells by electroporation. Briefly, ES cells are added to about 40 μg of Not I linearized targeting vector in 0.7 ml of culture medium using a BTX Transfector 100 at 250 V for 5 ms. Cells are plated at a density of $10^7$ cells/90 mm petri dish and at 12 hr post electroporation. One plate is trypsinized and the number of cells counted. This number is used to calculate the cell survival. G418 is added to the remaining cultures at a concentration of 150 mg/ml as well as 2 μM gancyclovir (GanC) at 24 hr post electroporation to enable the positive-negative selection of the recombination event. One plate is selected in the absence of GanC to evaluate the electroporation and the enrichment factor of the GanC selection. The number of colonies without GanC selection is deduced relative to this control.

After 10 days in selection media, single colonies are picked and grown in duplicate. To screen for homologous recombination events, crude cell lysates from one of the duplicates are subjected to PCR analysis. PCR analysis is performed using 25-30 mer oligonucleotides which are complementary to sequences located in the neo$^R$ gene and in the IL-2 receptor gene 3' to the targeting vector sequences. PCR is performed using 100 ng/reaction of each primer, 2U Taq polymerase (Cetus Corp., Emeryville, Calif.) and crude cell lysate (about 10,000 cells/reaction; (Kim and Smithies). The thermocycling is performed as follows: 40 cycles consisting of denaturation at 93° C. for 1 min, annealing at a temperature between 42° and 59° C. for 30 sec and polymerization at 72° C. for 2 min. Screening is performed using pools of eight clones. The single clones contained in the pools with the expected PCR product are rescreened by PCR to identify the actual recombinants. Positive clones are expanded further for Southern blot analysis. Blot analysis is performed using 5 μg of digested DNA per lane loaded onto a 0.8% agarose gel and transferred to nitrocellulose. The filter is hybridized to a probe complementary to the coding sequence of the IL-2 receptor and analyzed for the appropriate size fragment (Sambrook et al. and Ansubel et al.). The OtxIL2R ES cells are then used for in vitro differentiation and isolation of lineage specific neuronal stem cells (see section C below).

B. Construction of Stable Lines from Primordial Germ Cells Derived ES Cells

As with section A above, ES cell lines are constructed to express a reporter construct under the control of the Otx2 regulatory region. However, the ES cells used for these stable lines are derived from primordial germ cells of post implantation embryos (Matsui et al., supra).

Briefly, Sl$^4$-m220 feeder cells are maintained in Dulbecco's modified Eagles' medium (DMEM) with 10% calf serum and 50 μg/ml gentamycin. Cells are irradiated (500 rads) and plated at a density of $2\times10^5$ per well of a 24-well plate in the same medium 24 hrs before use. Wells are pretreated with 1% gelatin. To obtain primary cultures of primordial germ cells, ICR females are mated with (C57BL/

6×DBA) males embryos and the caudal region of 8.5–12.5 days post coitum (dpc) embryos is dissociated into single cells by incubation at 37° C. with 0.05% trypsin, 0.02% EDTA in $Ca^{2+}/Mg^{2+}$-free Dulbecco's phosphate-buffered saline for about 10 min with gentle pipetting. Cells from the equivalent of 0.5 embryos are seeded into a well containing feeder cells and 1 ml of DMEM, 2 mM glutamine, 1 mM sodium pyruvate, 100 IU/ml penicillin and 100 µg/ml streptomycin and 15% FCS. Growth factors are added at the time of seeding, usually at the following concentrations, recombinant human LIF and bFGF (10–20 ng/ml) and soluble rat SF (60 ng/ml) and the medium is changed every day. Primary cultures are trypsinized and reseeded into wells containing $Sl^4$-m220 feeder layers in PGC medium (above). For further subculture, rounded colonies of densely packed ES cells were carefully picked in a finely drawn pipette and trypsinized in a microdrop under mineral oil before seeding into wells containing feeder cells above. After several rounds of subculture the cells can be passaged without picking individual colonies.

The reporter construct used to stably transfect these ES cells is similar to that used with the blastocysts derived ES cells in that the reporter gene is a cell surface marker under the control of the Otx2 regulatory region. However, homologous recombination is not used to target the reporter gene to a specific locus and thus, only the $neo^R$ gene is required as a selectable marker. The reporter gene used for early neuronal expression is also the β-chain of the IL-2 receptor, however it is truncated just after the membrane spanning sequence and fused in frame to an immunoaffinity tag (Affimax). Although the IL-2 receptor is inactive without the γ-chain, this design ensures the loss of normal function of the IL-2 receptor when used as a surface tag.

To construct the expression construct, the IL-2 receptor cDNA is truncated at a convenient restriction site and fused in frame with the immunoaffinity tag. Alternatively, the immunoaffinity tag can be incorporated at the desired location using site directed mutagenesis or by PCR mutagenesis. The IL-2 receptor/immunoaffinity tag sequences are then ligated into the appropriate reading frame of the pcDNAINeo expression vector (Invitrogen, San Diego, Calif.). The promoter sequences of the expression vector are substituted with the Otx2 regulatory region for state specific expression of the reporter protein. The final construct is termed OtxIL2Af. Transfection into the above ES cells is performed by calcium-phosphate mediated transfection. Neomycin resistant colonies are picked, expanded and screened by PCR and RNase protection assay for intact OtxIL2Af construct sequences. All procedures described are well known to those skilled in the art and can be found in common laboratory manuals such as Sambrook et al. and Ansubel et at., supra. The OtxIL2Af ES cell lines are then used for in vitro differentiation and isolation of lineage specific neuronal stem cells (see section C below).

C. Isolation of Lineage Specific Neuronal Stem Cells Either the ES OtxIL2R or the ES OtxIL2Af cell lines are used in the methods below to isolate early stem cell of the neuronal cell lineage. Briefly, for in vitro differentiation into aggregates or embryoid body formation, ES cells are plated at a density of $10^7$ cells/100 mm bacterial petri dish in DMEM supplemented with 10% FCS and 0.1 mM β-mercaptoethanol. Culture medium is changed every day.

Isolation of early neuronal stem cells is performed by FACS isolation of the differentiating cultures taken at various time points. By 5 to 7 days in culture most of the aggregates differentiate into typical simple or cystic embryoid bodies with a clear outer layer of extraembryonic endoderm cells. When the embryoid bodies are returned to tissue culture plastic dishes they rapidly attach and give rise to a variety of cell types including extraembryonic endoderm, spontaneously contracting muscle, nerve and endothelial and fibroblast-like cells. Time points are taken both before (0–5 days) and after (6 14 days) returning to tissue culture plastic.

FACS isolation was performed using methods well known in the art. Briefly, cell aggregates are dissociated into single cells by treatment in $Ca^{2+}/Mg^{2+}$-free Dulbecco's phosphate-buffered saline plus 54 mM EDTA and washed in DMEM containing 10% FCS. The cells are then incubated on ice with an equal volume of a 1:50 dilution of the appropriate antibody ($1\times10^6$ cells in 0.1 ml) for 30 rain followed by a 10 ml wash in ice cold DMEM containing 10% FCS. Fluorescent conjugated secondary antibody is added at a dilution of 1:100 (0.1 ml) and again incubated on ice for an additional 30 min. The cells are washed once with 10 mls of ice cold DMEM containing 10% FCS and subjected to FACS isolation. Collected cells are plated in media allowed to proliferate. To prevent progression into terminally differentiated cell types various growth factors are assessed to maintain the potency of the early neuronal stem cells.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

REFERENCES

Ansubel et al., *Current Protocols in Molecular Biology*, John Whiley and Sons, Baltimore, Md. (1989).

Biesecker and Emerson, "Interleukin-6 is a Component of Human Umbilical Curd Serum and Stimulates Hematopoiesis in Embryonic Stem Cells in vitro" *Exp. Hematology* 21:774–778 (1993).

Chisaka, O. and Capecchi, M. R., "Regionally Restricted Developmental Defects Resulting from Targeted Disruption of the Mouse Homeobox Gene Hax-1.5" *Nature* 350:473–479 (1991).

Dinsmore et at., "High Efficiency Differentiation of Mouse Embryonic Stem Cells into Either Neurons or Skeletal Muscle in vitro" Keystone Symposium (Abstract H111) *J. Cell. Biochem.* Supplement 18A:177(1994).

Fleming et at., "Functional Heterogeneity is Associated with the Cell Cycle Status of Murine Hematopoietic Stem Cells" *J. Cell Biol.* 122:897–902 (1993).

Groves et at., "Repair of Demyelinated Lesions by Transplantation of Purified O–2A Progenitor Cells" *Nature* 362:453–455 (1993).

Hooper et at., "HPRT-Deficient (Lesch-Nyhan) Mouse Embryos Derived from Germline Colonization by Cultured Cells" *Nature* 326:292–295 (1987).

Jones et al., "Separation of Pluripotent Hematopoietic Stem Cells from Spleen Colony-Forming Cells" *Nature* 347:188–189 (1990).

Jones and Watt, "Separation of Human Epidermal Stem Cells from Transit Amplifying Cells on the Basis of Differences in Integrin Function and Expression" *Cell* 73:713–723 (1993).

Keller et al., "Hematopoietic Commitment During Embryonic Stem Cell Differentiation in Culture" *Mol. Cell. Biol.* 13:473–486 (1993).

Kim and Smithies, "Recombinant Fragment Assay for Gene Targeting Based on the Polymerase Chain Reaction" *Nucleic Acids. Res.* 16:8887–8903 (1988).

Lillien and Raft, "Differentiation Signals in the CNS: Type-2 Astrocyte Development in vitro as a Model System" *Neuron* 5:111–119 (1990).

Lufkin et al., "Disruption of the Hax-1.6 Homeobox Gene Results in Defects in a Region Corresponding to its Rostral Domain of Expression" *Cell* 66:1105–1119 (1991).

Mansour et al., "Introduction of a LacZ Reporter gene into the Mouse int-2 Locus by Homologous Recombination" *Proc. Natl. Acad. Sci. USA* 87:7688–7692 (1990).

Matsui et al., "Derivation of Pluripotential Embryonic Stem Cells from Murine Primordial Germ Cells in Culture" *Cell* 70:841–847 (1992).

McKay, R., "The Origins of Cellular Diversity in the Mammalian Central Nervous System" *Cell* 58:815–821 (1989).

McMahon et al., "The Midbrain-Hindbrain Phenotype of Wnt-1⁻/Wnt-1⁻ Mice Results from Stepwise Deletion of engrailed-Expressing Cells by 9.5 Days Postcoitum" *Cell* 69:581–595 (1992).

Otl et al., "Use of Recombinant Embryonic Stem Cells to Isolate Neural Stem Cells" Keystone Symposium (Abstract H222) *J. Cell. Biochem.* Supplement 18A:177 (1994).

Patterson, P., "Control of Cell Fate in a Vertebrate Neurogenic Lineage" *Cell* 62:1035–1038 (1990).

Porteus et at., "Isolation and Characterization of a Novel cDNA Clone Encoding a Homeodomain That is Developmentally Regulated in the Ventral Forebrain" *Neuron* 7:221–229 (1991).

Price et at., "A Mouse Gene Related to distal-less Shows a Restricted Expression in the Developing Forebrain" *Nature* 351:748–751 (1991).

Resnick et al., "Long-Term Proliferation of Mouse Primordial Germ Cells in Culture" *Nature* 359:550–551 (1992).

Reynolds and Weiss, "Generation of Neurons and Astrocytes from Isolated Cells of the Adult Mammalian Central Nervous System" *Science* 255:1707–1710 (1992).

Roelink, H. and Nuse, R., "Expression of Two Members of the Wnt Family During Mouse Development-Restricted Temporal and Spatial Patterns in the Developing Neural Tube" *Genes Dev.* 5:381–388 (1991).

Sambrook et al., Molecular Cloning: A Laboratory Manual, Cold Spring Harbor Laboratory, New York (1992).

Schmitt et al., "Hematopoietic Development of Embryonic Stem Cells in vitro: Cytokine and Receptor Gene Expression" *Genes and Develop.* 5:728–740 (1991).

Simeone et at., "Nested Expression Domains of Four Homeobox Genes in Developing Rostral Brain" *Nature* 358:687–690 (1992).

Simeone et al., "Two Vertebrate Homeobox Genes Related to the Drosophila empty spiracles Gene are Expressed in the Embryonic Cerebral Cortex" *EMBO J.* 11:2541–2550 (1992).

Snodgrass et at., "Embryonic Stem Cells and in vitro Hematopoiesis" *J. Cell. Biochem.* 49:225–230 (1992).

Stemple and Anderson, "Isolation of a Stem Cells for Neurons and Glia from the Mammalian Neural Crest" *Cell* 71:973–985 (1992).

Wagner, E., "On Transferring Genes into Stem Cells and Mice" *EMBO J.* 9:3025–3032 (1990).

Wolswijk and Noble, "Identification of an Adult-Specific Glial Progenitor Cell" *Development* 105:387–400 (1989).

What is claimed is:

1. A method of isolating a lineage specific stem cell in vitro, comprising:
   a. transfecting in vitro a pluripotent embryonic stem cell with a construct comprising a regulatory region of a lineage specific gene operably linked to a DNA encoding a reporter protein;
   b. culturing the pluripotent embryonic stem cell in vitro under conditions such that the pluripotent embryonic stem cell differentiates into a lineage specific stem cell; and
   c. separating the cells fluorescent activated cell sorting or by immunoaffinity procedures which express the reporter protein from the other cells in culture, the cell which expresses the reporter protein being an isolated lineage specific stem cell.

2. The method of claim 1 wherein the regulatory region of the lineage specific gene is selected from the group consisting of an Otx, Dlx, Nlx, Emx, Wnt, En, Hox and ACHRβ.

3. The method of claim 1 wherein the reporter protein is a protein expressed on the cell surface.

4. The method of claim 1 wherein the reporter protein is LacZ.

5. A method of isolating a lineage specific stem cell in vitro, comprising:
   a. transfecting in vitro a pluripotent embryonic stem cell with a construct comprising a regulatory region of a lineage specific gene operably linked to a DNA encoding a reporter protein;
   b. culturing the pluripotent embryonic stem cell in vitro under conditions which allow the formation of aggregates of differentiating cells; and
   c. separating the cells by fluorescent activated cell sorting or by immunoaffinity procedures in the aggregates which express the reporter protein from the other cells, the cell which expresses the reporter protein being an isolated lineage specific stem cell.

6. The method of claim 5 wherein the aggregates are cultured to form embryoid bodies prior to separating the cells.

7. The method of claim 5 wherein the regulatory region of the lineage specific gene is selected from the group consisting of an Otx, Dlx, Nlx, Emx, Wnt, En, Hox and ACHRβ.

8. The method of claim 5 wherein the reporter protein is expressed on the cell surface.

9. The method of claim 5 wherein the reporter protein is LacZ.

* * * * *